(12) United States Patent
Ivarsson et al.

(10) Patent No.: US 10,768,108 B2
(45) Date of Patent: Sep. 8, 2020

(54) SURFACE PLASMON RESONANCE BIOSENSOR SYSTEM

(71) Applicant: GE HEALTHCARE BIO-SCIENCES AB, Uppsala (SE)

(72) Inventors: Bengt Ivarsson, Balinge (SE); Stefan Sjolander, Uppsala (SE)

(73) Assignee: GE HEALTHCARE BIO-SCIENCES AB, Uppsala (SE)

( * ) Notice: Subject to any disclaimer, the term of this patent is extended or adjusted under 35 U.S.C. 154(b) by 0 days.

(21) Appl. No.: 14/342,868

(22) PCT Filed: Sep. 27, 2012

(86) PCT No.: PCT/SE2012/051022
§ 371 (c)(1),
(2) Date: Mar. 5, 2014

(87) PCT Pub. No.: WO2013/048318
PCT Pub. Date: Apr. 4, 2013

(65) Prior Publication Data
US 2014/0227136 A1    Aug. 14, 2014

(30) Foreign Application Priority Data
Sep. 28, 2011    (SE) ...................... 1150890

(51) Int. Cl.
*G01N 21/552* (2014.01)
*G01N 33/543* (2006.01)

(52) U.S. Cl.
CPC ......... *G01N 21/554* (2013.01); *G01N 21/553* (2013.01); *G01N 33/54373* (2013.01)

(58) Field of Classification Search
CPC ......... G01N 33/54373; G01N 33/0031; G01N 21/553; G01N 21/554
(Continued)

(56) References Cited

U.S. PATENT DOCUMENTS

| 5,035,863 | A | | 7/1991 | Finlan et al. |
| 5,313,264 | A | * | 5/1994 | Ivarsson et al. ............... 356/73 |

(Continued)

FOREIGN PATENT DOCUMENTS

| EP | 0305109 A1 | 3/1989 |
| EP | 0341927 B1 | 7/1993 |

(Continued)

OTHER PUBLICATIONS

PCT/SE2012/051022 ISRWO dated Jan. 21, 2013.
(Continued)

*Primary Examiner* — Dennis White
*Assistant Examiner* — Bryan Kilpatrick
(74) *Attorney, Agent, or Firm* — Culhane Meadows, PLLC; Jeff V. Vockrodt

(57) ABSTRACT

A Surface Plasmon Resonance (SPR) biosensor system comprising: a SPR sensor surface, an illumination unit arranged to direct a wedge shaped beam of light at a line shaped detection area on the SPR sensor surface transverse to the direction of propagation of light, and a detection unit with detection optics for directing light reflected from the SPR sensor surface onto a two-dimensional optical detector unit such that the angle of reflection is imaged along one dimension and the width of the detection area along the other, wherein the illumination unit is arranged to selectively direct the wedge shaped beam of light at two or more spaced apart line shaped detection areas on the SPR sensor surface transverse to the direction of propagation of light.

15 Claims, 14 Drawing Sheets

(58) Field of Classification Search
USPC ..... 422/69, 82.05, 82.11, 501, 502; 436/164
See application file for complete search history.

(56) References Cited

U.S. PATENT DOCUMENTS

| | | | |
|---|---|---|---|
| 5,917,607 | A | 6/1999 | Naya |
| 5,923,031 | A | 7/1999 | Naya |
| 6,268,125 | B1 | 7/2001 | Perkins |
| 6,270,657 | B1 | 8/2001 | Graham et al. |
| 6,570,657 | B1 * | 5/2003 | Hoppe et al. ............... 356/445 |
| 6,738,141 | B1 | 5/2004 | Thirstrup |
| 7,811,515 | B2 | 10/2010 | Malmqvist et al. |
| 2004/0165188 | A1 | 8/2004 | Anafi et al. |
| 2005/0084980 | A1 * | 4/2005 | Koo et al. ................... 436/171 |
| 2006/0227328 | A1 | 10/2006 | Vanwiggeren et al. |
| 2009/0010589 | A1 | 1/2009 | Robertson |
| 2010/0238443 | A1 | 9/2010 | Claypool et al. |

FOREIGN PATENT DOCUMENTS

| | | | |
|---|---|---|---|
| EP | 1157266 | A1 | 11/2001 |
| EP | 0863395 | B1 | 6/2005 |
| GB | 2197068 | A * | 5/1988 |
| JP | 02017431 | A | 1/1990 |
| JP | 09-292332 | A | 11/1997 |
| JP | 11-051857 | A | 2/1999 |
| JP | 2001-504582 | A | 4/2001 |
| JP | 2002536638 | A | 10/2002 |
| JP | 2006-113021 | A | 4/2006 |
| JP | 2008-070391 | A | 3/2008 |
| WO | 9522754 | A1 | 8/1995 |
| WO | 9822808 | A1 | 5/1998 |
| WO | 2005046859 | | 5/2005 |
| WO | 2009078510 | | 6/2009 |

OTHER PUBLICATIONS

Suzuki, et.al. Development of novel optical waveguide surface plasmon resonance (SPR) sensor with dual light emitting diodes, Sensors: and Actuators B: Chemical: international journal devoted to research and development of physical and chemical transducers, vol. 106 NR 1, pp. 383-387, Apr. 29, 2005.
European Search Report for European Application No. 12836996.4 dated May 7, 2015.
Japanese Office Action for JP Application No. 2014-533242 dated Aug. 2, 2016 (4 pages).
Kretschmann, E., "The ATR Method with Focused Light—Application in Guided Waves on Grating", Optics Communications, vol. 26, pp. 41-44, 1978.
Benner. K.M., "Angular Emission Profiles of Dye Molecules Excited by Surface Plasmon Waves at a Metal Surface", Optics Communications, vol. 30, pp. 145-149, 1979.
Swalen, J. D. et al., "Plasmon Surface Polariton Dispersion by Direct Optical Observation", American Journal of Physics, vol. 48, pp. 669-672, 1980.

* cited by examiner

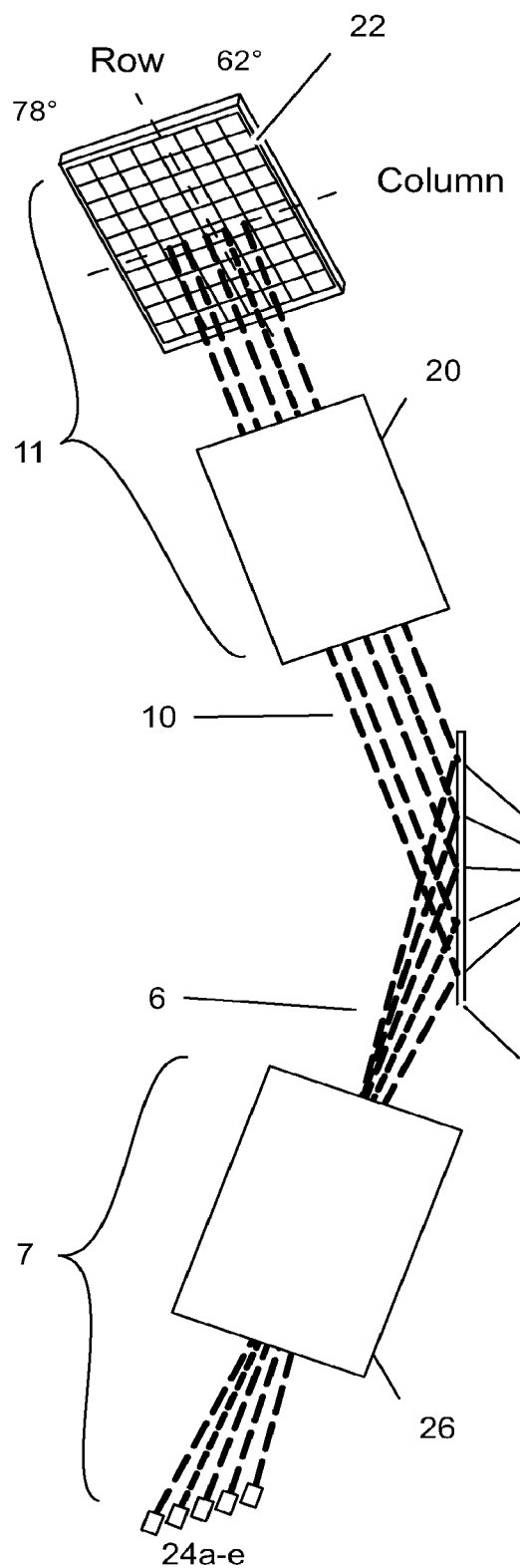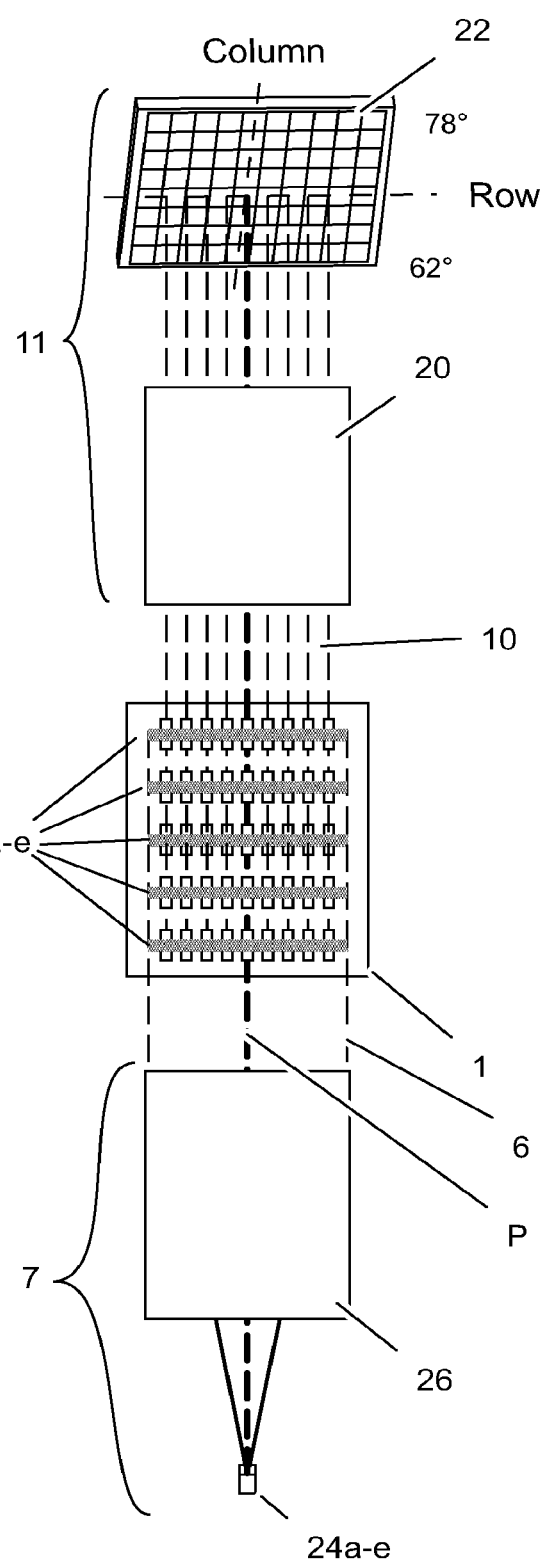
Fig. 14a
Fig. 14b

SURFACE PLASMON RESONANCE BIOSENSOR SYSTEM

This application is a filing under 35 U.S.C. 371 of international application number PCT/SE2012/051022, filed Sep. 27, 2012, which claims priority to Sweden application number 1150890-0 filed Sep. 28, 2011, the entire disclosure of which is hereby incorporated by reference.

FIELD OF THE INVENTION

The present invention relates to a Surface Plasmon Resonance (SPR) biosensor system, and more particularly to a highly sensitive SPR biosensor system with increased capacity.

BACKGROUND OF THE INVENTION

Surface Plasmon Resonance (SPR) biosensor systems that can monitor interactions between molecules, such as biomolecules, in real time are maintaining increasing interest. A representative such biosensor system is the BIACORE® instrumentation sold by GE Healthcare which uses surface plasmon resonance (SPR) for detecting interactions between molecules in a sample and molecular structures immobilized on a sensing surface. As sample is passed over the sensor surface, the progress of binding directly reflects the rate at which the interaction occurs. Injection of sample is followed by a buffer flow during which the detector response reflects the rate of dissociation of the complex on the surface. A typical output from the BIACORE® system is a graph or curve describing the progress of the molecular interaction with time, including an association phase part and a dissociation phase part. This binding curve, which is usually displayed on a computer screen, is often referred to as a "sensorgram".

As was published by Kretschmann, E., Optics Communications, 26, (1978) 41-44, the problem of slow speed of operation relative to changes in reflectance and the insufficient precision in the resonance angle determination related with SPR procedures based on moveable mechanics, is solved by the use of a fan-shaped beam (equivalent to several beams simultaneously incident upon the sensor surface over a range of angles) and of collection of the reflected beams (over a range of angles) by an array of angularly spaced detectors.

Furthermore, the transparent block described in EP-A1-0 305 109 may take the form of a hemicylinder creating a wedge-shaped beam, giving a line of a small illuminated area on the sensing surface. The hemicylindrical lens has the advantage that it can be used to perform several tests simultaneously on a single sample. To this end, the sensing surface takes the form of a series of sensitive areas (1D array of sensor spots), each comprising a different antibody, with each separate area being monitored by its own detector in a detector array. The cylindrical focusing principle used to produce an identical angular range of light beams along a focused line for SPR of separate surface areas has been published by Benner, R. E. et al. Optics Communications 30 (1979) 145-149, and Swalen, J D et al. Am J. Phys. 48 (1980) 669-672.

SUMMARY OF THE INVENTION

The object of the invention is to provide a new SPR biosensor system, which SPR biosensor system overcomes one or more drawbacks of the prior art 2D spot array SPR detection. This is achieved by the SPR biosensor system as defined in the independent claims.

One advantage with the method of the present invention is that it allows increased number of detector spots for interaction studies in a robust, simple, low-cost, and efficient way.

A more complete understanding of the present invention, as well as further features and advantages thereof, will be obtained by reference to the following detailed description and drawings.

BRIEF DESCRIPTION OF THE DRAWINGS

FIGS. 9 to 14 show alternative embodiments of the present invention.

DETAILED DESCRIPTION OF THE INVENTION

As mentioned above, the present invention relates to A Surface Plasmon Resonance (SPR) biosensor system comprising:

a SPR sensor surface, an illumination unit arranged to direct a wedge shaped beam of light at a line shaped detection area on the SPR sensor surface transverse to the direction of propagation of light, and a detection unit with detection optics for directing light reflected from the SPR sensor surface onto a two-dimensional optical detector unit such that the angle of reflection is imaged along one dimension and the width of the detection area along the other, wherein the illumination unit is arranged to selectively direct the wedge shaped beam of light at two or more spaced apart line shaped detection areas on the SPR sensor surface.

Before describing the present invention in more detail, however, the general context in which the invention is intended to be used will be described.

Unless defined otherwise, all technical and scientific terms used herein have the same meaning as commonly understood by a person skilled in the art related to this invention. Also, the singular forms "a", "an", and "the" are meant to include plural reference unless it is stated otherwise.

All publications, patent applications, patents, and other references mentioned herein are incorporated by reference in their entirety.

Commercially available biosensors include the aforementioned BIACORE® system instruments, manufactured and marketed by GE Healthcare, which are based on surface plasmon resonance (SPR) and permit monitoring of surface binding interactions in real time between a bound ligand and an analyte of interest. In this context, "ligand" is a molecule that has a known or unknown affinity for a given analyte and includes any capturing or catching agent immobilized within the sensing volume (detection volume) at the surface, whereas "analyte" includes any specific binding partner thereto.

The phenomenon of SPR is well known, suffice it to say that SPR arises when light is reflected under certain conditions at the interface between two media of different refractive indices, and the interface is coated by a metal film, typically silver or gold. In the BIACORE® instruments, the media are the sample and the glass of a sensor chip which is contacted with the sample by a microfluidic flow system. The metal film is a thin layer of gold on the chip surface. SPR causes a reduction in the intensity of the reflected light at a specific angle range of reflection. The angle of minimum reflected light intensity, so-called SPR-angle, varies with the refractive index close to the metal surface on the side opposite from the reflected light, in the BIACORE® system the sample side.

Figure 1:
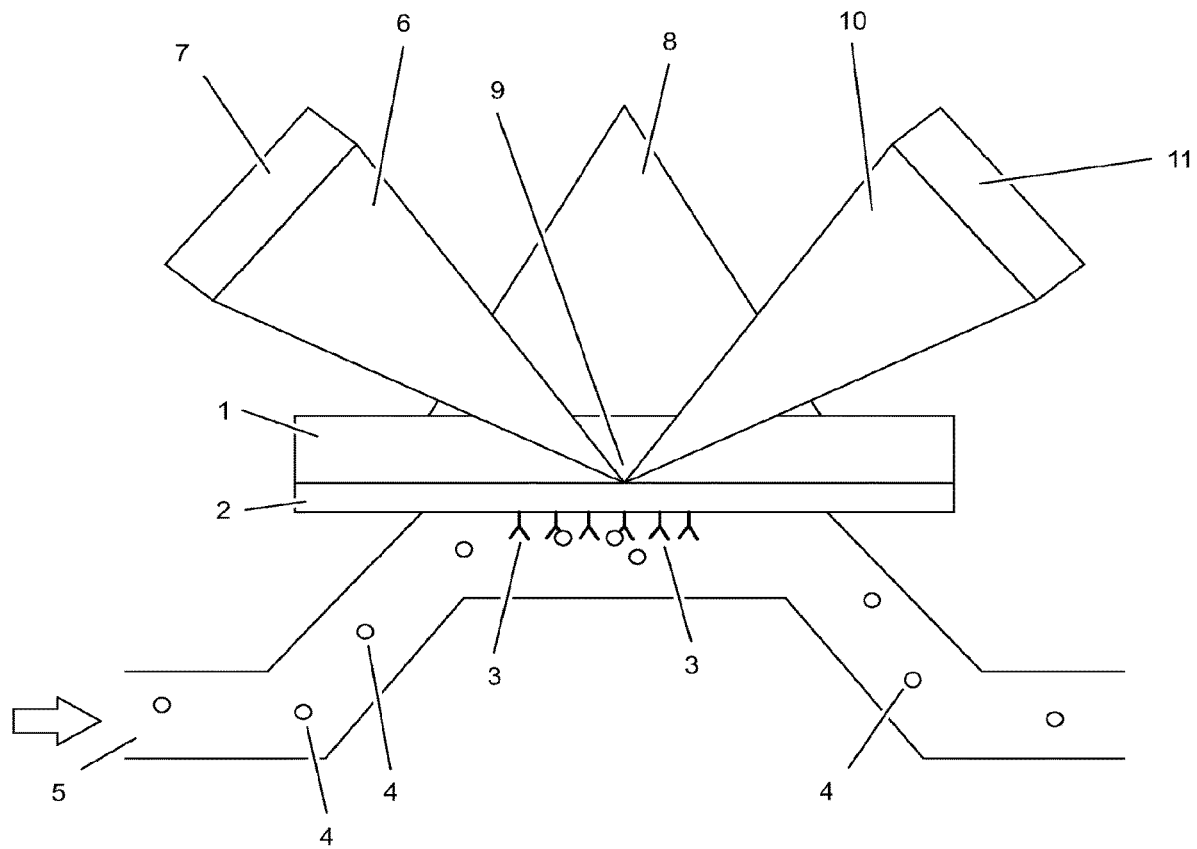
FIG. 1 is a schematic side view of a biosensor system based on SPR.

A schematic illustration of the BIACORE® system is shown in FIG. 1. Sensor chip 1 has a gold film 2 supporting capturing molecules (ligands) 3, e.g. antibodies, exposed to a sample flow with analytes 4, e.g. an antigen, through a flow channel 5. Mainly monochromatic p-polarised light 6 from an illumination unit 7 (e.g. LED) is coupled by a prism 8 to the glass/metal interface 9 where the light undergoes attenuated total reflection due to the SPR, forming the SPR-curve. The intensity of the reflected light beam 10 is detected by an optical detection unit 11 (e.g. a photodetector array).

When molecules in the sample bind to the capturing molecules on the sensor chip surface, the concentration, and therefore the refractive index at the surface changes and an SPR response, change in SPR-angle, intensity, or SPR-curve shape parameter, due to the shift in SPR-curve angular position, is detected. Plotting the response against time during the course of an interaction will provide a quantitative measure of the progress of the interaction. Such a plot, or kinetic or binding curve (binding isotherm), is usually called a sensorgram, also sometimes referred to in the art as "affinity trace" or "affinogram". In the BIACORE® system, the SPR response values are expressed in resonance units (RU). One RU represents a change of 0.0001° in the angle of minimum reflected light intensity, or SPR-curve centroid angle, which for most proteins and other biomolecules correspond to a change in concentration of about 1 $pg/mm^2$ on the sensor surface. As sample containing an analyte contacts the sensor surface, the capturing molecule (ligand) bound to the sensor surface interacts with the analyte in a step referred to as "association." This step is indicated on the sensorgram by an increase in RU as the sample is initially brought into contact with the sensor surface. Conversely, "dissociation" normally occurs when the sample flow is replaced by, for example, a buffer flow. This step is indicated on the sensorgram by a drop in RU over time as analyte dissociates from the surface-bound ligand.

Figure 2:
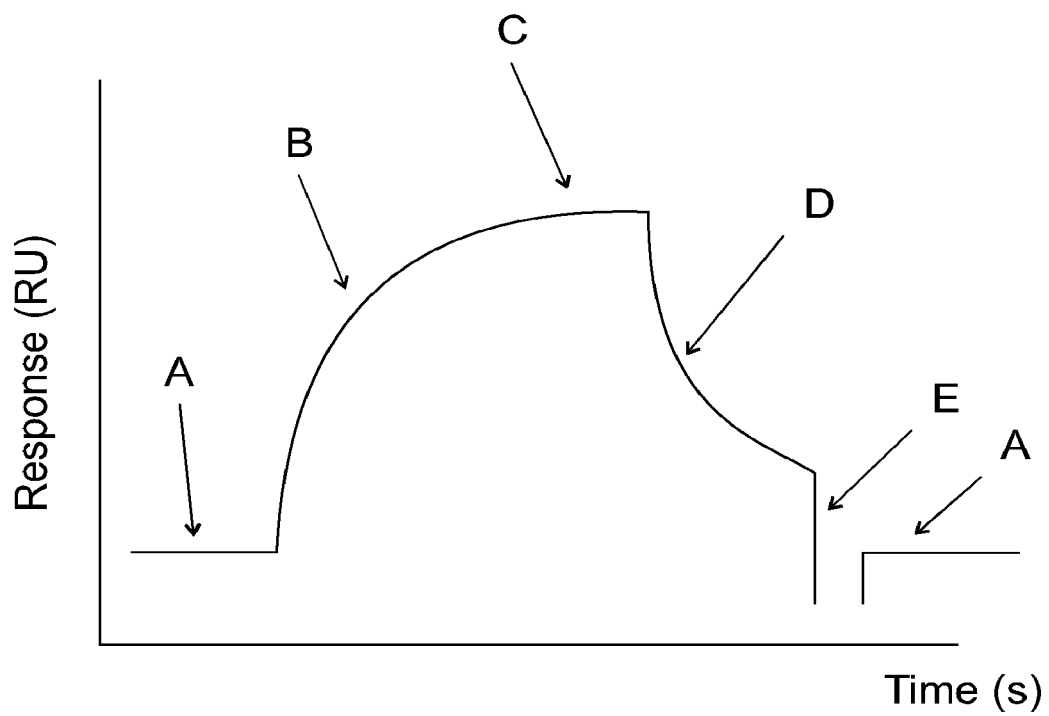
FIG. 2 is a representative sensorgram where the binding curve has visible association and dissociation phases.

A representative sensorgram (binding curve) for a reversible interaction at the sensor chip surface is presented in FIG. 2, the sensing surface having an immobilised capturing molecule, or ligand, for example an antibody, interacting with a binding partner therefor, or analyte, in a sample. The vertical axis (y-axis) indicates the response (here in resonance units, RU) and the horizontal axis (x-axis) indicates the time (here in seconds). Initially, buffer is passed over the sensing surface giving the baseline response A in the sensorgram. During sample injection, an increase in signal is observed due to binding of the analyte. This part B of the binding curve is usually referred to as the "association phase". Eventually, a steady state condition is reached at or near the end of the association phase where the resonance signal plateaus at C (this state may, however, not always be achieved). It is to be noted that herein the term "steady state" is used synonymously with the term "equilibrium" (in other contexts the term "equilibrium" may be reserved to describe the ideal interaction model, since in practice binding could be constant over time even if a system is not in equilibrium). At the end of sample injection, the sample is replaced with a continuous flow of buffer and a decrease in signal reflects the dissociation, or release, of analyte from the surface. This part D of the binding curve is usually referred to as the "dissociation phase". The analysis is ended by a regeneration step where a solution capable of removing bound analyte from the surface, while (ideally) maintaining the activity of the ligand, is injected over the sensor surface. This is indicated in part E of the sensorgram. Injection of buffer restores the baseline A and the surface is now ready for a new analysis.

From the profiles of the association and dissociation phases B and D, respectively, information regarding the binding and dissociation kinetics is obtained, and the height of the resonance signal at C represents affinity (the response resulting from an interaction being related to the change in mass concentration on the surface). This will now be explained in more detail below.

A detailed discussion of the technical aspects and the basic optical principles of BIACORE® instruments and the phenomenon of SPR may be found in U.S. Pat. No. 5,313,264.

Figure 3A:
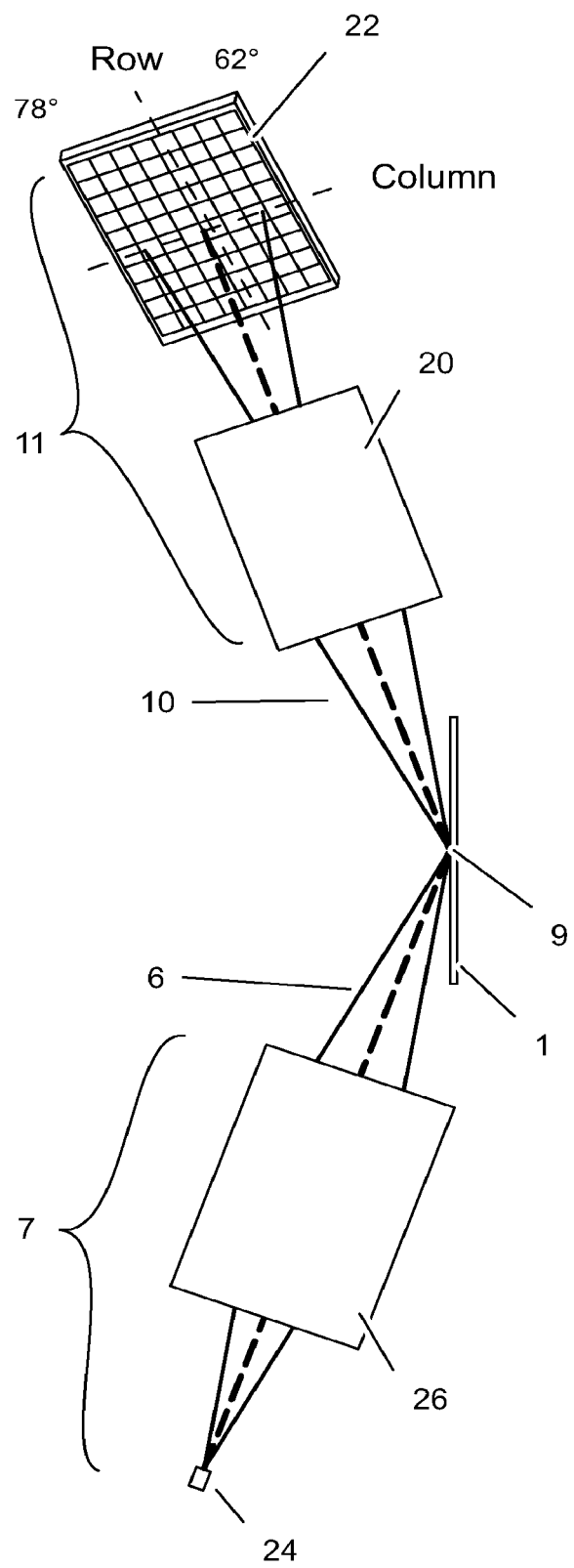
FIGS. 3a and 3b show a schematic view of a prior art SPR biosensor system.
Figure 3B:
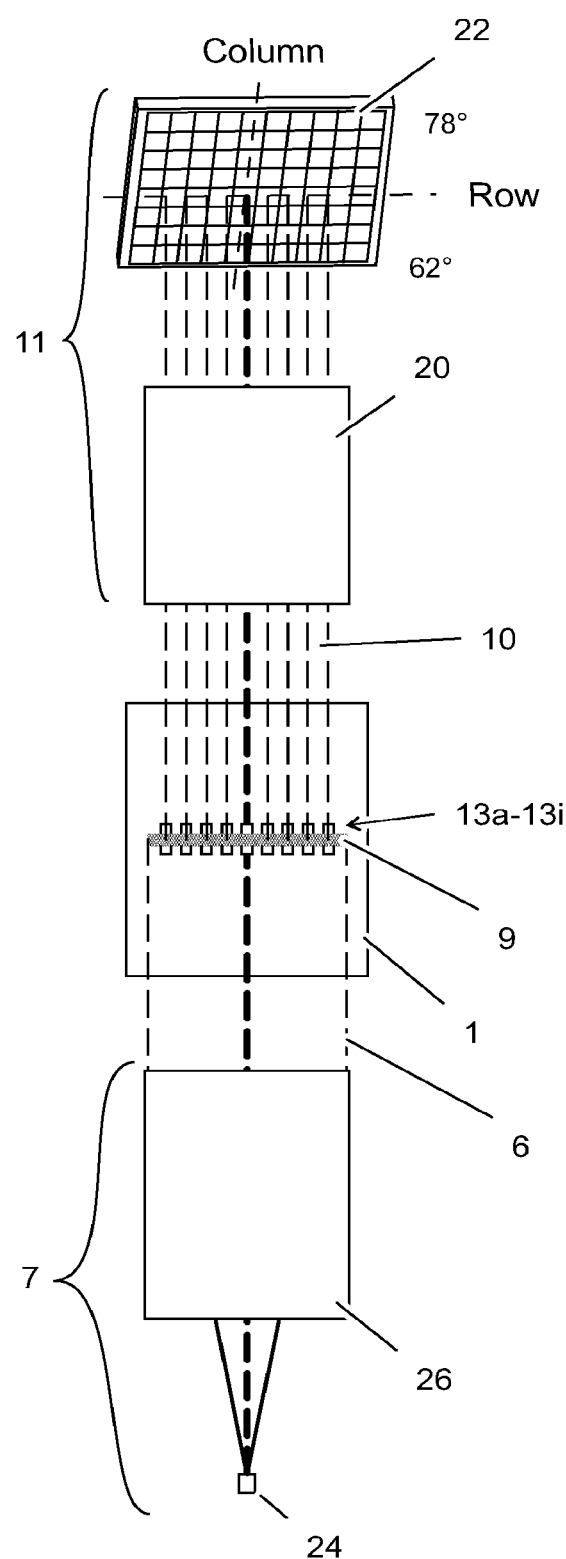

FIGS. 3a and 3b schematically illustrate the optical system in such a prior art BIACORE® system, where FIG. 3b is a top view and FIG. 3a is a cross-sectional side view of the plane P in FIG. 3b. Such systems comprises an illumination unit 7 comprising a light source 24 and wedge forming optics 26, arranged to direct a wedge shaped beam of light 6 at a line shaped detection area 9 on the SPR sensor surface 2 transverse to the direction of propagation of light. For illustrative purposes, all refractive elements in the light path have been omitted (e.g. optics for coupling the beam to the sensor surface like a prism as is shown in FIG. 1) or replaced by general "optics" units (e.g. 20 and 26). The wedge shaped beam of light 6 is essentially uniform in the transverse direction as illustrated in FIG. 3b, and strikes the illustrated line shaped detection area 9 at angles of incidence relevant for SPR detection such as from 62 to 78 degrees. Rays with all the intermediate (e.g. between 62° and 78 degree) angles of incidence are present in the beam. The system further comprises a detection unit 11 with special, anamorphic detection optics 20 for directing light reflected from the SPR sensor surface 1 onto a two-dimensional optical detector unit 22 such that the angle of reflection is imaged along one dimension (column) and the width of the detection area along the other (row). For illustration purposes, consider only one incident plane, light incident e.g. at 62° is reflected on the sensitized surface 9 and is imaged by the detection optics 20 on only one single detection element 28A of the two-dimensional optical detector unit 22. Similarly, light incident with an angle of 78° will be imaged on one single detection element 28H. Light having incident angle values intermediate between 62 and 78 degrees will similarly strike those single detection elements which are situated between elements 28A and 28H in the same detector column; in FIGS. 3a and 3b this is illustrated as being a vertical column.

The light source 24, e.g. a light emitting diode, emits a type of light that is substantially monochromatic in character (bandwidth~50 nm), and furthermore is incoherent and has a center wavelength of an order of magnitude of about 650 to about 850 nm. Alternatively, the light source 24 is a laser, e.g. a semiconductor laser, a dye laser or a gas laser, emitting substantially monochromatic and coherent light. The light source 24 may also take the form of a low coherent edge emitting diode like either a superluminescent or superradiant diode (SLD), or an ELED.

Light rays having a different plane of incidence parallel to the plane of incidence P will in a similar way be imaged on individual detection elements belonging to other columns of the two-dimensional optical detector unit 22. Every detection element of a row thus corresponds to one specific angle of incidence. Thus to each column of the two-dimensional optical detector unit 22 corresponds a respective part of the sensing surface as seen in the transverse direction of the conduit portion. Depending on the width of the sample flow channel, the magnification of the detection optics, the surface dimensions of the individual detection elements, and the spaces between them, a particular number of detection element columns may be required for imaging the total width of the flow channel portion in question.

In the embodiment of FIGS. 3a and 3b, nine detection spots 13a-13i for interaction analysis are illustrated allowing registration of up to nine independent interactions simultaneously. As is well established in the art, a ligand is immobilized on each detection spot (one or more spots may intentionally be left without ligand to serve as a reference channel for mitigating non-specific contributions to the SPR response) and the same or different analytes are brought into contact with the sensor spots. According to one embodiment, as is shown in U.S. Pat. No. 5,313,264, each detection spot 13 is associated with a flow channel for passing the analyte over the spot, but alternatively two or more detection spots 13 may be arranged in one single flow cell e.g. capable of hydrodynamic addressing of individual detection spots 13 (as is disclosed in U.S. Pat. No. 7,811,515).

In the prior art systems of the type shown in FIGS. 3a and 3b, the max theoretical number of detection spots is limited by the number, of pixel rows on the two-dimensional optical detector unit 22, while the practical number depends on the size of the detection spots 13 and associated fluidic system.

Figure 4A:
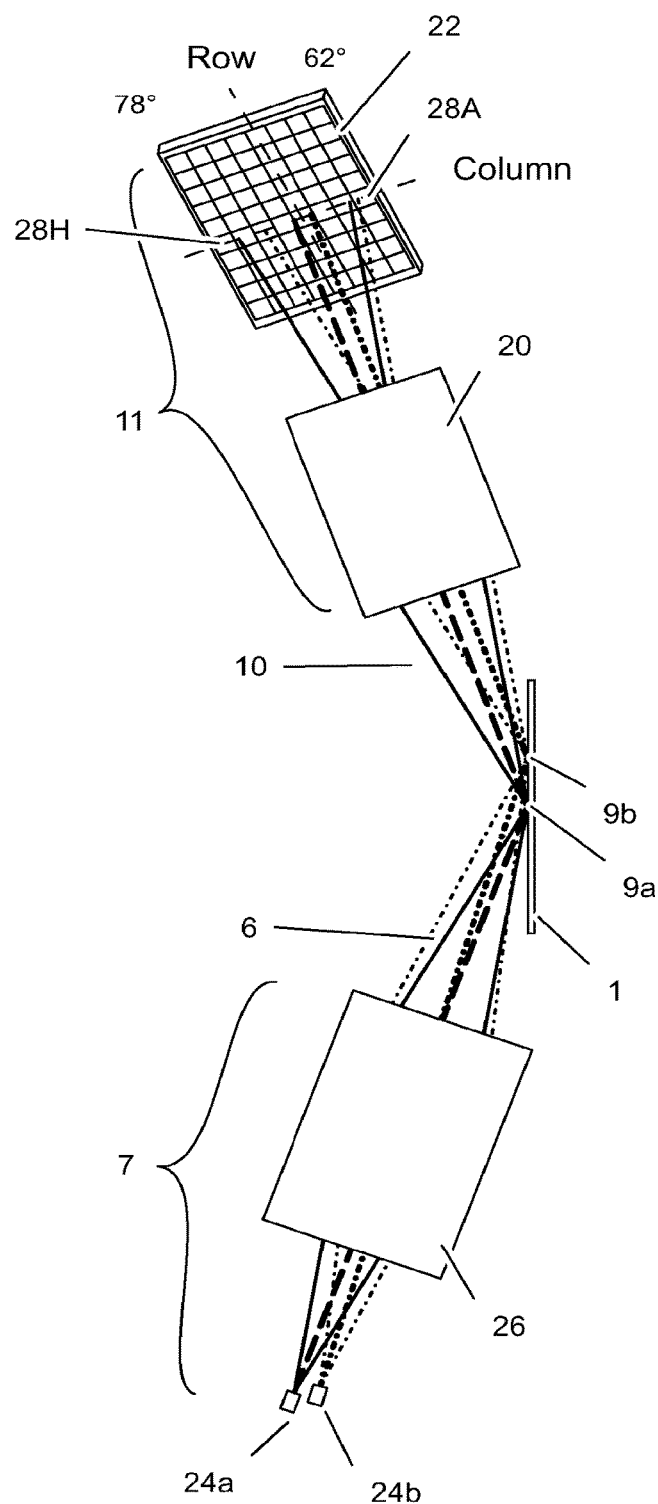
FIGS. 4a and 4b show a schematic view of one embodiment of a SPR biosensor system of the present invention.
Figure 4B:
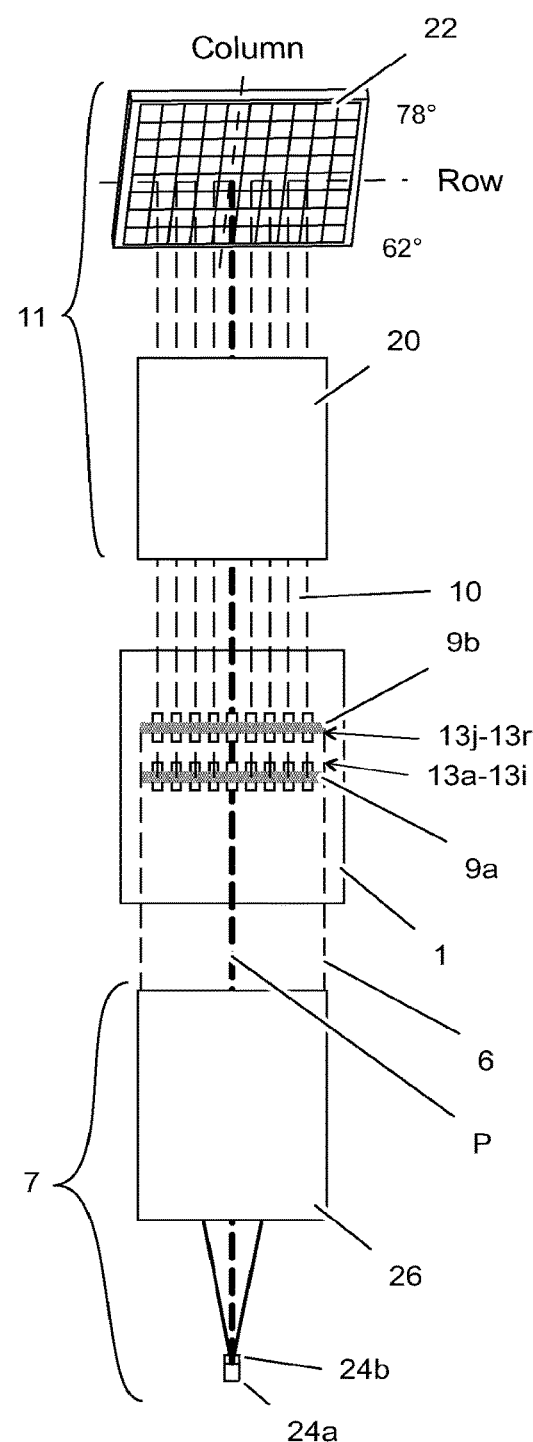

FIGS. 4a and 4b shows a schematic embodiment of a Surface Plasmon Resonance (SPR) biosensor system according to one embodiment of the present invention, wherein the number of detection spots 13 is doubled without the need to significantly redesign the optics of the system. By providing a second light source 24b spaced apart from the first light source 24a by a suitable distance in the plane P, and suitably controlling the emission of light from the light sources, the illumination unit is arranged to selectively direct the wedge shaped beam of light 6 at two spaced apart line shaped detection areas 9a and 9b, respectively, on the SPR sensor surface 1 transverse to the direction of propagation of light. In general, all elements of the prior art SPR system of FIGS. 3a and 3b may be left unchanged, but as will be appreciated by a person skilled in the art there may be optimizations available. It shall be noted that the displacement of the second light source 24b and the associated beam paths is exaggerated for illustrative purposes, and the real displacement in a working optical design may be very small to achieve a suitable distance between the detection areas 9a and 9b on the sensor surface. The real displacement may further be restricted by the optical properties (e.g. aperture/imaging area) of all other optical components along the path.

According to one embodiment containing two light sources 24a and 24b about 0.3 mm apart, two light beams could be generated at the same time giving two detection areas 9a and 9b about 1 mm apart on the sensor surface 1.

Figure 5A:
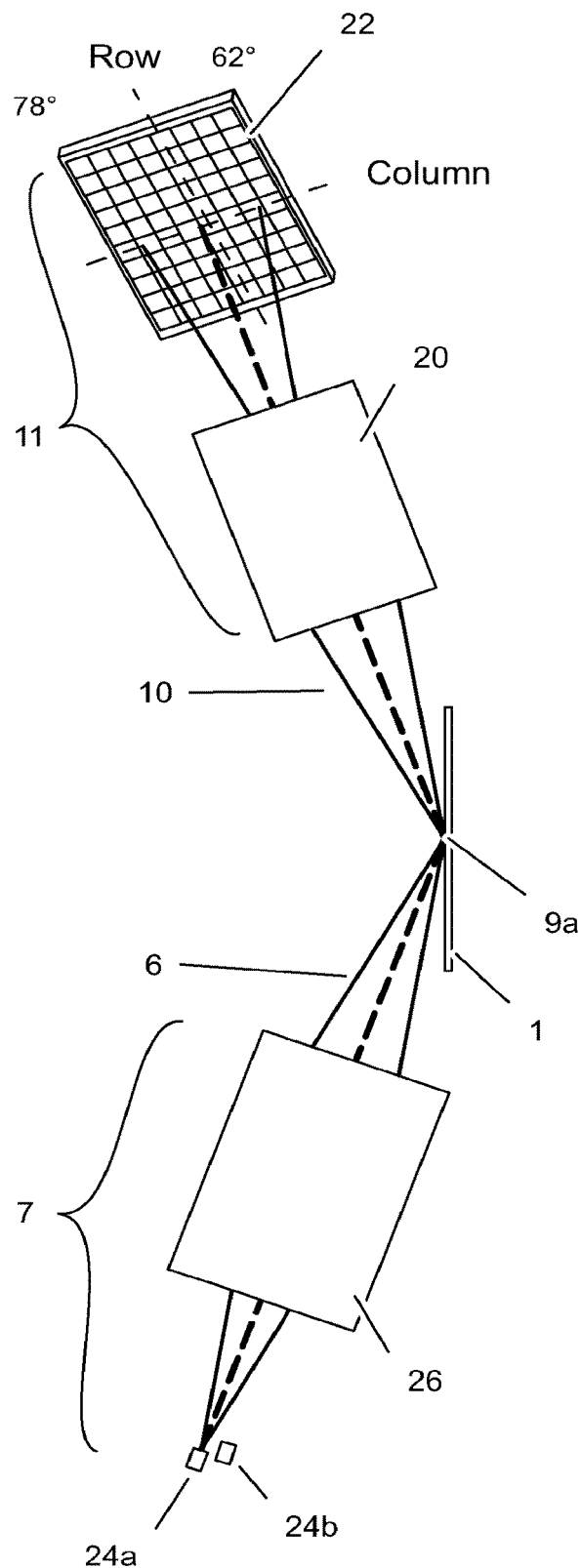
FIGS. 5a and 5b illustrates the working principle of the SPR biosensor system of FIGS. 4a and 4b
Figure 5B:
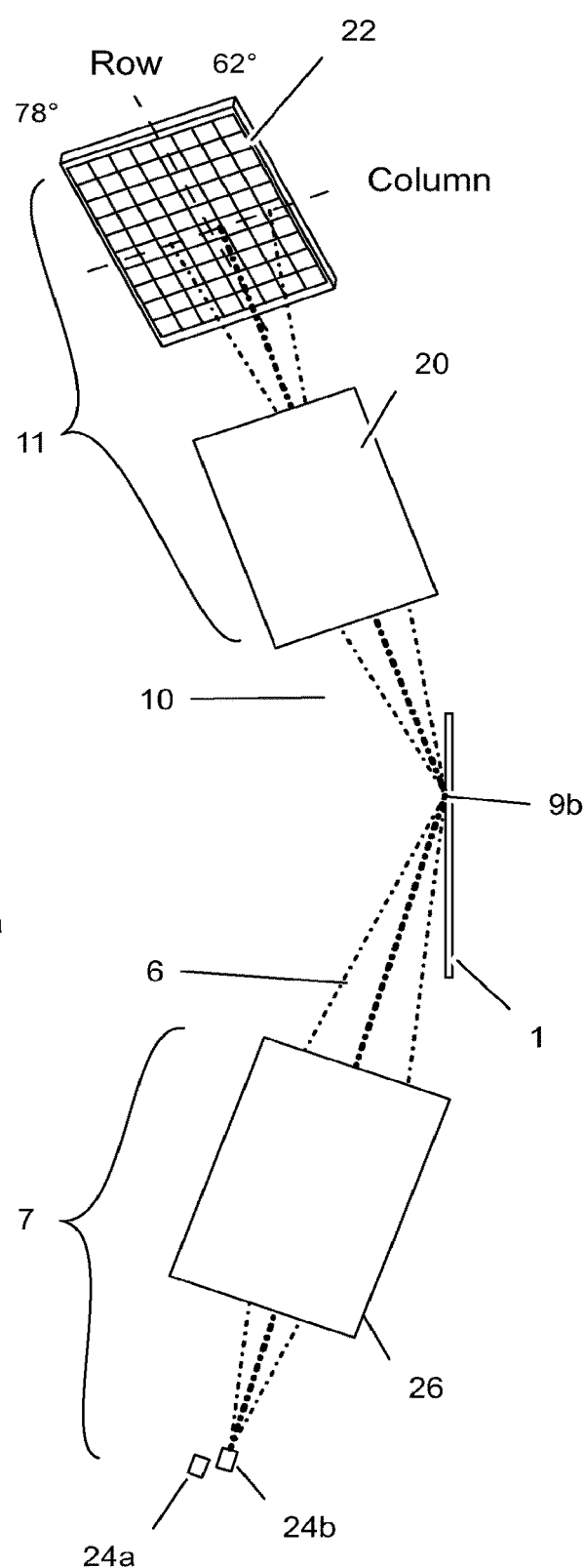

Since the two detection areas 9a and 9b for each detection spot 13 pair (spots arranged in the same plane parallel to the plane P) will be imaged onto the same pixel column on the two-dimensional optical detector unit 22 the two interaction responses measured as one SPR-curve (one dip in the reflectance curve) at the time, cannot be registered completely simultaneous. Therefore, in order to register interaction data independently from detection spots 13 along the two detection areas 9a and 9b, the two light sources 24a and 24b are alternately switched on and off at a suitable frequency, in synchronization with the readout from the two-dimensional optical detector unit 22. By this, two nearly simultaneous sets of sensorgrams can be generated, one for each of the two detection spot-rows. Alternate switching on and off of the two light sources 24a and 24b is illustrated in FIGS. 5a and 5b.

In some applications, two detection areas 9a and 9b for each detection spot 13 pair (spots arranged in the same plane parallel to the plane P) may be simultaneously imaged onto the same pixel column on the two-dimensional optical detector unit 22, thus forming an overlaid SPR-curve containing at least two reflectance minima. This enables for a completely simultaneous monitoring of the relative interaction response between said detection areas, measured as a shift between said two reflectance minima. In such an embodiment, the SPR evaluation unit is arranged to measure relative SPR-angle shifts from combined readings of SPR-curves (multi reflectance dips) for light reflected from the two or more spaced apart line shaped detection areas.

Figure 6:
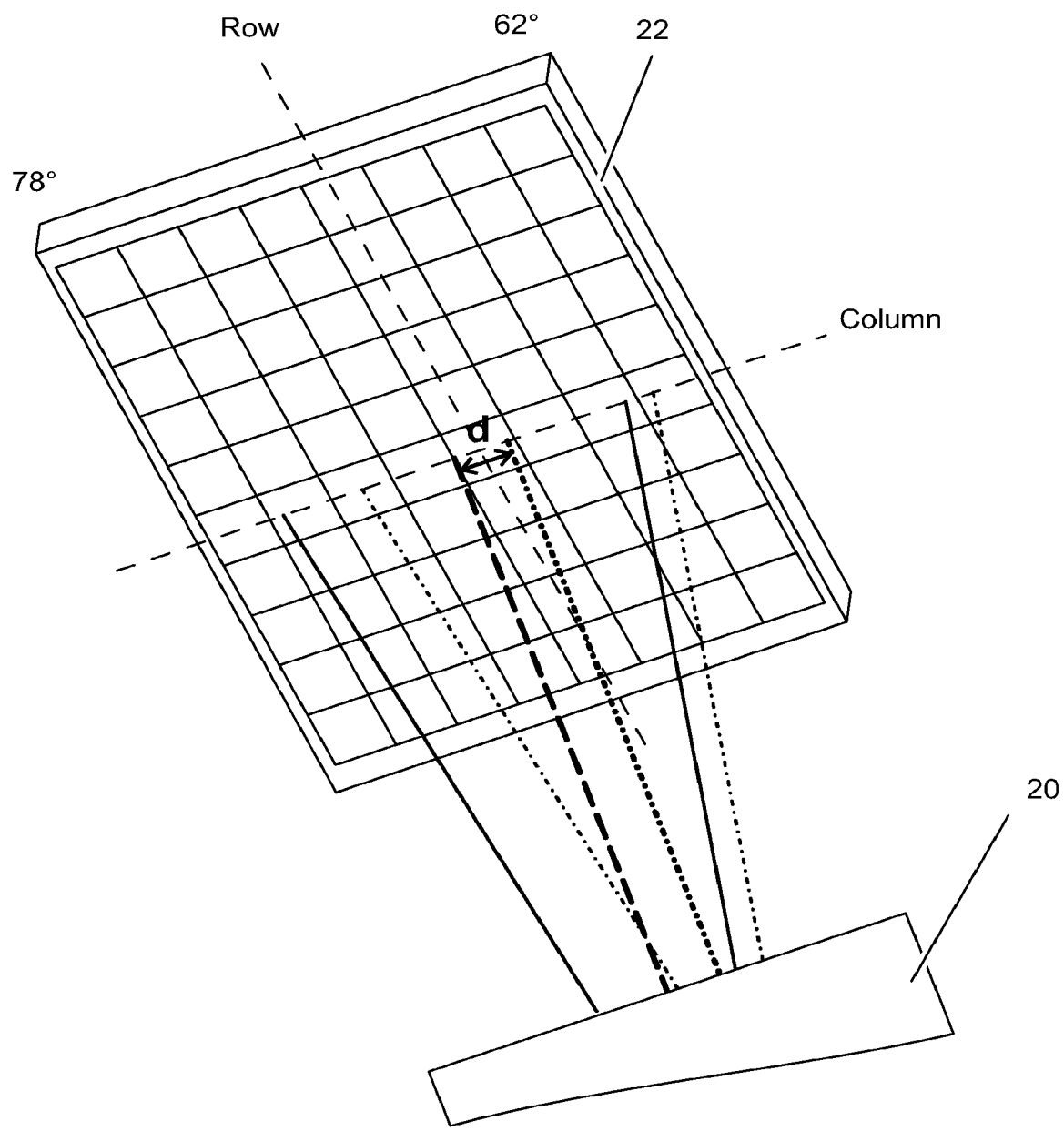
FIGS. 6 to 8 show enlarged sections of the SPR biosensor system of FIGS. 4a and 4b

As can be seen in FIGS. 4a-5b, due to the vertical displacement in plane P of the light sources, the angle of incidence ranges will differ slightly for the two wedge shaped beams. According to the above embodiment with the light sources displaced about 0.3 mm apart, the angle of incidence range will differ in the order of 0.2°, thus, being 62.0° to 78.0° for detection area 9b, while 61.8° to 77.8° for detection area 9a. Hence, there will be a small offset between the angular ranges alternately imaged onto a pixel column. Said offset in angular range is more clearly illustrated in the enlarged view of the two-dimensional optical detector unit 22 in FIG. 6, wherein the offset in angular range for the image of the wedge shaped beam center ray 6 is denoted d, which according to the above embodiment is e.g as small as 0.2°. However, due to the angle-to-point "imaging" of the anamorphic detection optics (as disclosed in detail in U.S. Pat. No. 5,313,264) in plane P, there will be no offset between the pixel column positions for SPR curves encoding an identical refractive index at spots along said focal lines. And moreover, there will be no offset between the pixel column positions corresponding to a respective part of the sensing surface as seen in the transverse direction for the two parallel detection areas 9a and 9b. According to one embodiment, the two or more wedge shaped beams include rays providing an approximately identical absolute angle of incidence range. (e.g. wedge beam nr 1: 65°-75°, wedge beam nr 2: 65°-75°). According to another embodiment the two or more wedge shaped beams include rays providing wedge shaped beams of more than one absolute angle of incidence range (e.g. wedge beam nr 1: 65°-75°, wedge beam nr 2: 62°-78°, whereby the angular dynamic range differs for the two beams). Still according to another embodiment, the two or more wedge shaped beams include rays providing wedge shaped beams of more than one non-overlapping absolute angle of incidence range (e.g. wedge beam nr 1: 60°-70°, wedge beam nr 2: 70°-80°, whereby the absolute angle range differs for the two beams). The different angular intervals may be achieved by different positioning of the light sources 24a and b, and the design of the wedge forming optics 26.

Figures 7A, 7B:
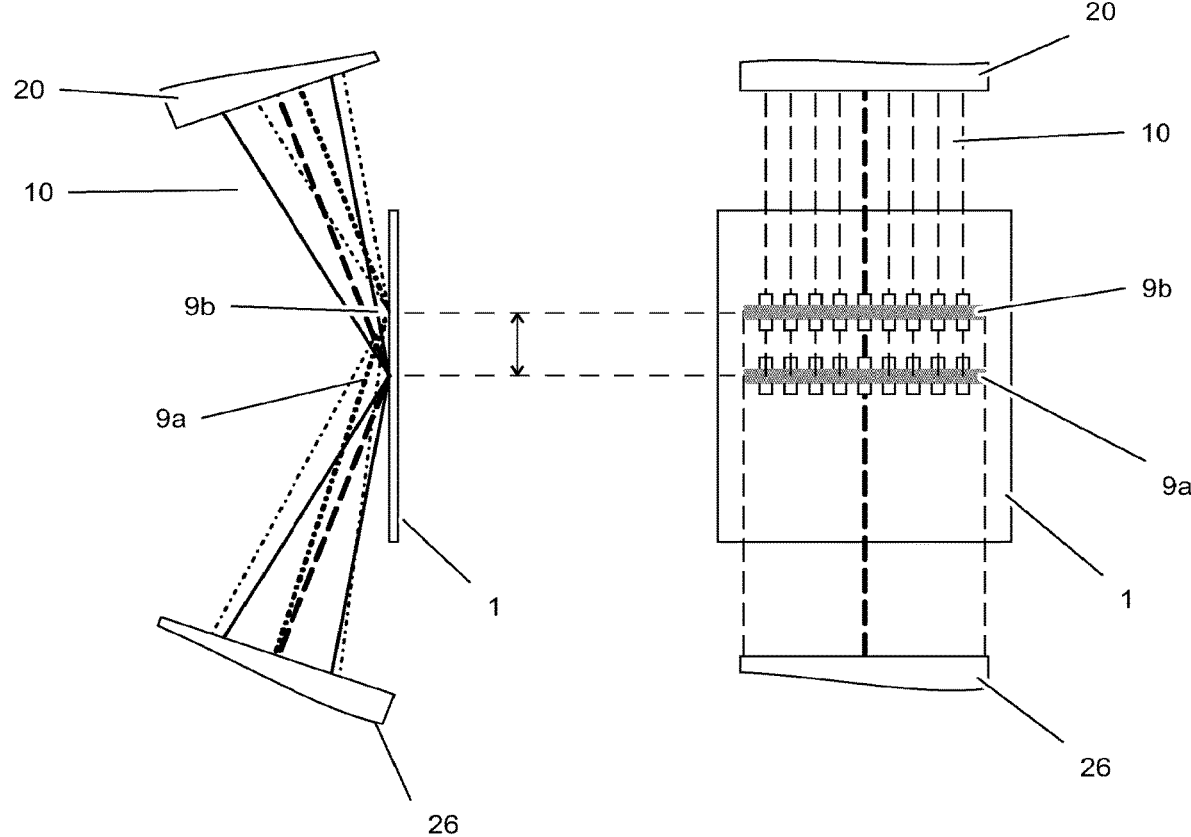
Figure 8:
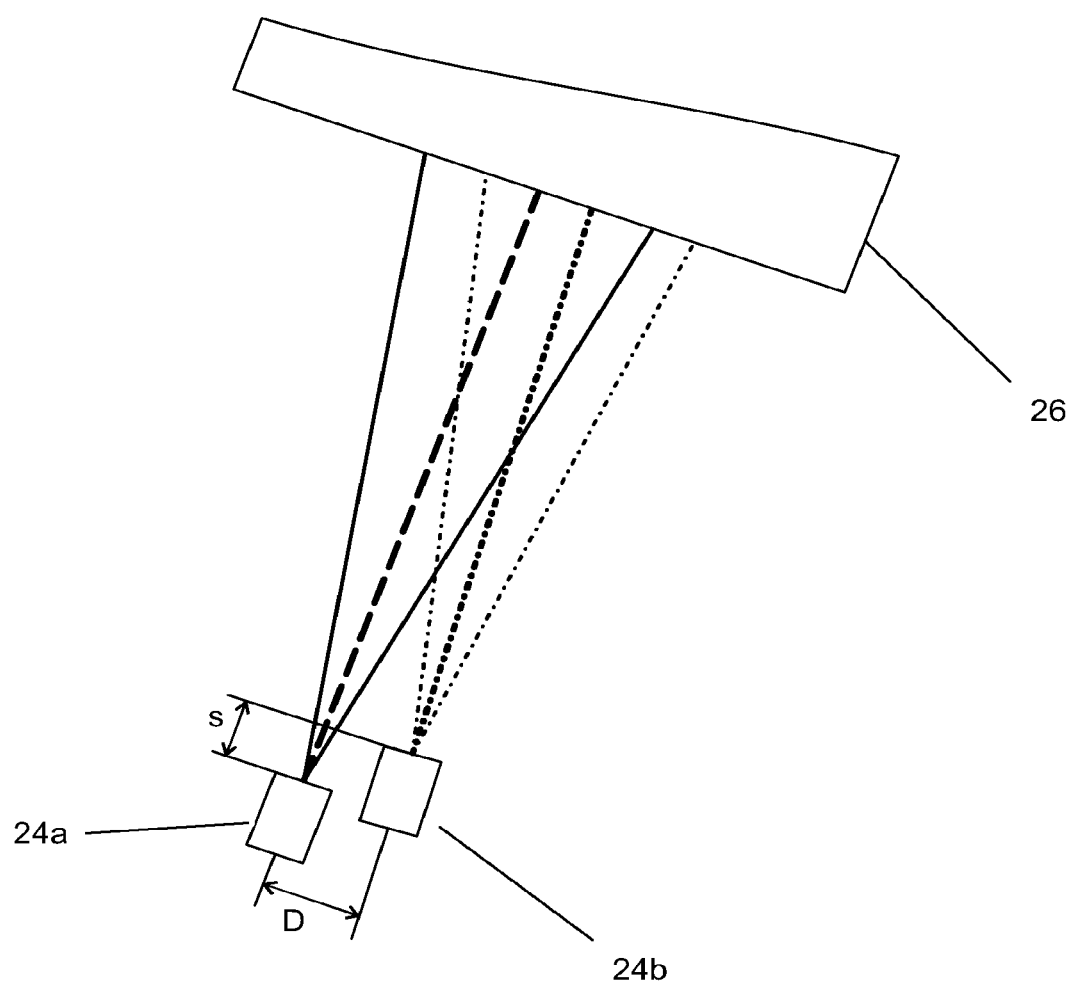

FIGS. 7a and 7b shows enlarged views of the SPR sensor surface 1 with the two beam arrangement of FIGS. 4a and 4b, and FIG. 8 shows an enlarged view of the arrangement with two light sources 24a and 24b. The relative positioning of the two light sources 24a and 24b is highly dependent on the optical properties of the wedge shaping optics 26. In order to achieve best possible sensitivity and performance, the wedge shaped beams 6 associated with each one of the light sources 24a and 24b should strike the sensor surface 1 to form detection areas 9a and 9b of the same width, and the width should be suitably narrow. According to one embodiment, each wedge shaped beam 6 associated with a light source 24a or 24b, should strike the sensor surface essentially at its "focal point". Taken that a vertical displacement, indicated by D in FIG. 8, of the second light source 24b results in a horizontal (along the general direction of propagation of the light) displacement of the position where the associated beam 6b strikes the sensor surface 1 (e.g. detection area 9b), the distance between the wedge forming optics 26 and the detection area 9b increases. Therefore the focal point of the associated beam 6b preferably is correspondingly displaced by a lateral displacement of the light source 24b as indicated by s in FIG. 8.

Figure 9:
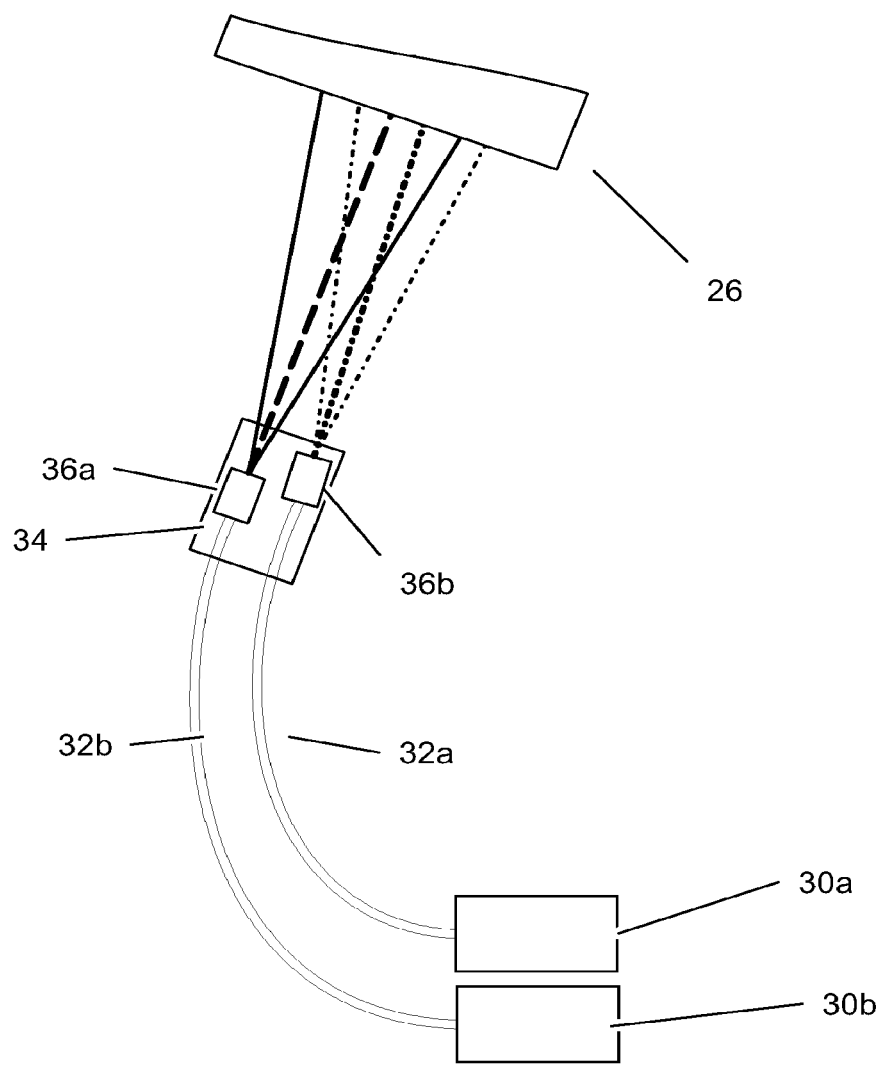
Figure 10:
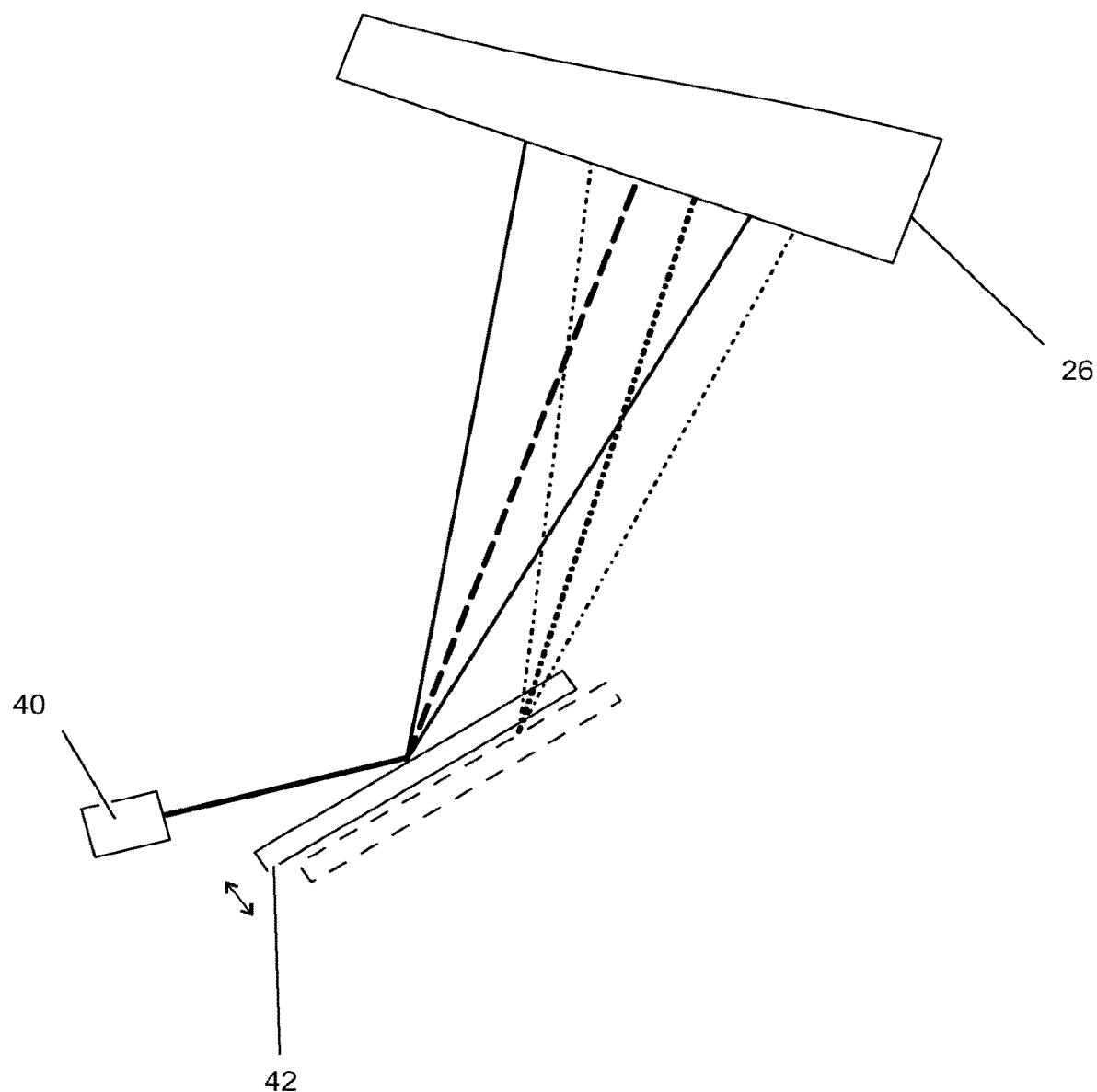

The light sources 24a and 24b may e.g. be comprised of small sources of light that can be mounted sufficiently close in order to achieve the desired effect. According to one embodiment, the light sources 24a and 24b are LED chips or edge-emitting superluminescent diode (SLD) light sources. According to another embodiment, the two or more light sources may be comprised of two or more optical wave guides or light pipes with their exit surfaces closely mounted and each connected to external light sources, as is schematically disclosed in FIG. 9, the two or more optical wave guides are comprised of two optical fibers 32a and 32b closely mounted in a ferrule 34 and connected to external light sources 30a and 30b. In such an embodiment, two or more light sources (LEDs, SLDs, ELEDs, Laser diodes) may be sequentially switched on and off according to above, or they may be continuously emitting light, and their optocoupling to the optical fibers, waveguides, or light pipes contains means for alternatively switching the passage of light on and off at a suitable frequency, in synchronization with the readout from the two-dimensional optical detector unit.

According to one embodiment, the means the means for alternatively switching the passage of light on and off comprises a lens and a light beam shutter positioned between each light source and receiving end of to the respective optical fiber, waveguide, or light pipe such that the light passage between either the light source and lens, or the lens and said receiving end may be selectively blocked by the beam shutter. The beam shutter(s) may be an electro-mechanical or electro-optical shutter. According to another embodiment, the means for alternatively switching the passage of light on and off may comprise a moveable mirror positioned between each light source and receiving end of fiber/waveguide/light pipe such that the light passage between the light source and said receiving end may be alternatively free/blocked by an electro-mechanical mirror.

Figure 11:
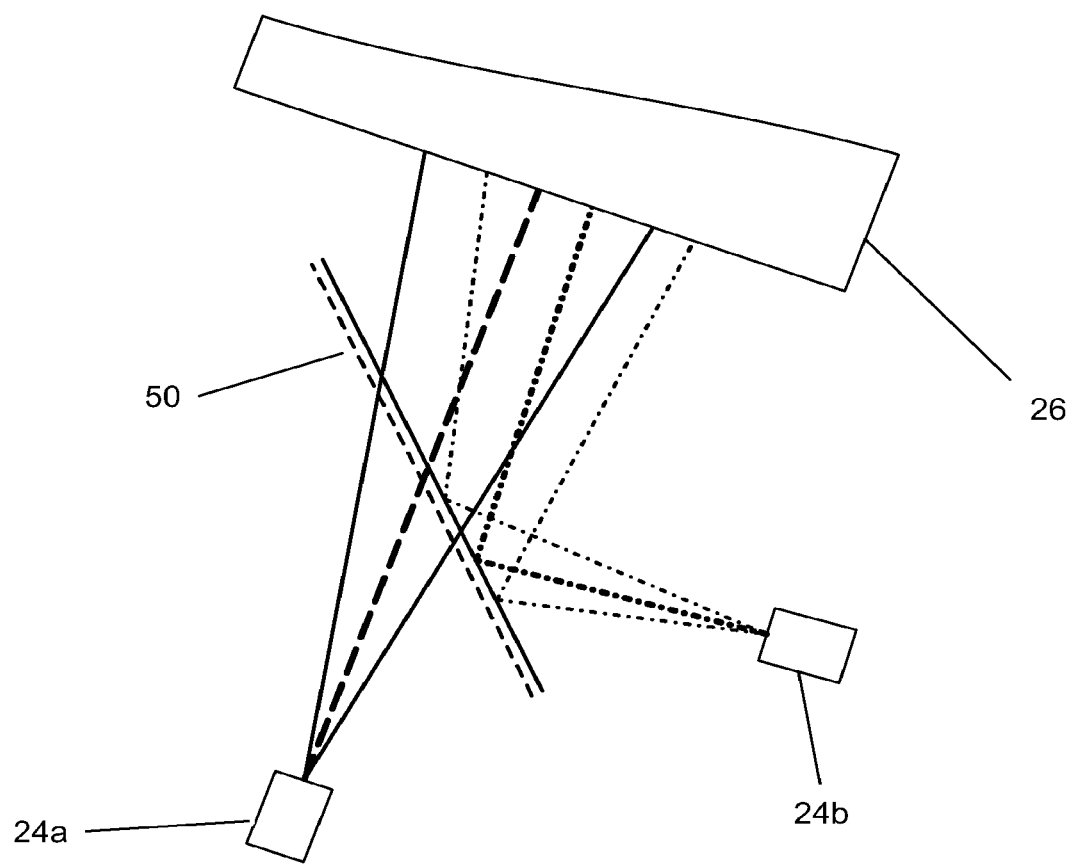

According to one embodiment, the two or more light sources are comprised of two or more LEDs, ELEDs, SLDs, or laser diodes which beams, coming either directly from each light source or via a beam collimator, beam collector, or beam condenser at each light source, are combined by use of a beam combining arrangement positioned in the light path before the static illumination optics that forms the wedge shaped beam. According to one embodiment, schematically disclosed in FIG. 11, the beam combining arrangement may comprise a semi-transparent mirror 50 arranged to combine the beams from the two light sources 24a and 24b at the static illumination optics 26. The semi-transparent mirror may be comprised of e.g. a transparent substrate slide which surface is coated by a semi-transparent/reflective metal film, or of a reversely used optical beam splitter device (e.g., prism, plate or membrane). Said mirror transmits a part of one light source light beam intensity in the direction towards the static illumination optics, while it reflects a part of a second light source beam intensity in the direction towards the static illumination optics.

Figure 12:
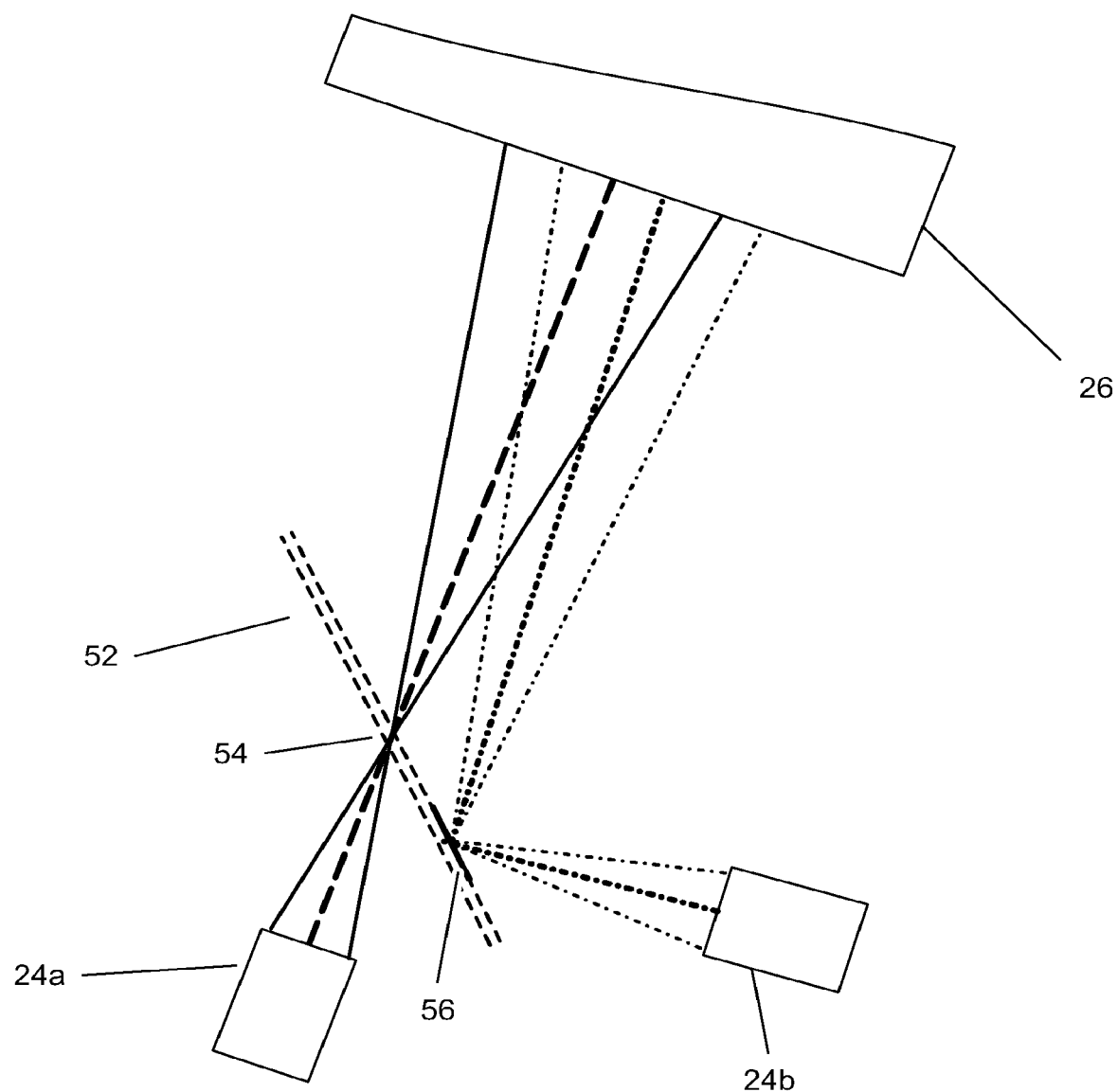

According to one embodiment, schematically disclosed in FIG. 12, the beam combining arrangement may comprise an optical body 52 which is divided into one transparent part 54 and one reflective part 56, wherein the optical body transmits one light source 24a light beam in the direction towards the static illumination optics while it reflects a second light source 24b light beam in the direction towards static illumination optics 26. Alternatively, the optical body may be limited to the reflective part 56 whereby the light beam from the first light source 24a does not have to pass through the optical body but besides the same. The lengths and angles for the optical axes together with the degree of beam collimation (or divergence), and relative position of the spherically focused beams onto said beam combiner is chosen to provide a suitable operating angle of incidence range for each of the two wedge shaped beams incident to the sensor surface at the two parallel and separated focal lines.

Figure 13:
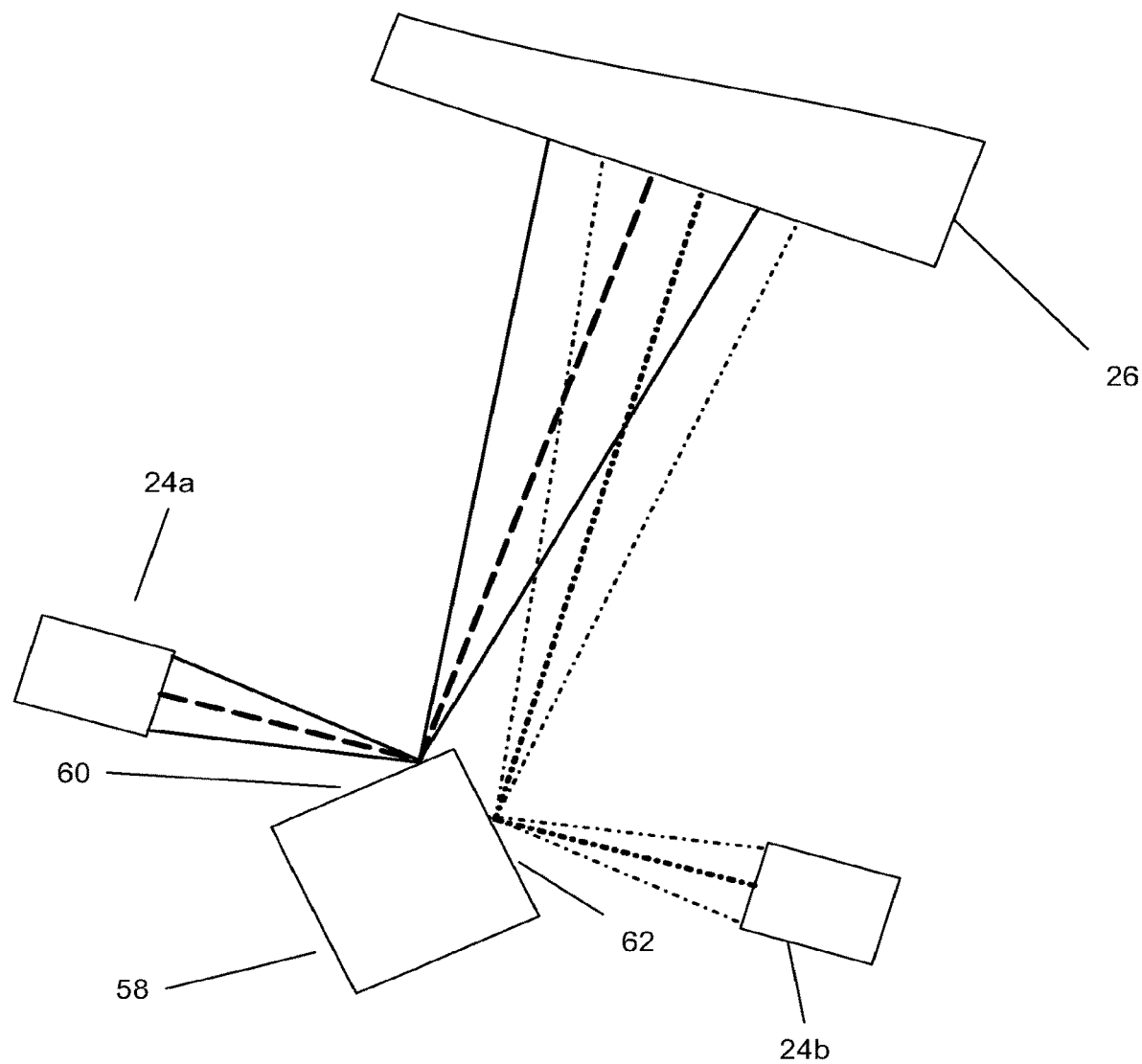

According to one embodiment, schematically disclosed in FIG. 13, the beam combining arrangement may comprise an optical body 58 which is divided into different reflective parts 60 and 62 respectively, each arranged to reflect the light beam of one light source 24a or 24b in the direction towards static illumination optics 26.

In still a further embodiment, the two light sources are replaced by a light source and a light beam translation unit, such as a moveable mirror arrangement 42 for selectively translating a light beam from a single light source 40 in a direction transverse to the direction of propagation into two or more positions.

As previously mentioned, the present design does not need to be limited to two detection areas 9a and 9b, and FIGS. 14a and 14b discloses an embodiment with 5 parallel detection areas 9a to 9e, hence providing 45 detection spots 13.

According to one embodiment, the illumination unit may comprise one or more light sources 24a and 24b of different wavelengths with respect to each other in order to to provide a first wedge shaped beam of a first wavelength at the first line shaped detection area 9a, and a second wedge shaped beam of a second wavelength at the second line shaped detection area 9b. By such arrangement, different properties of investigated interactions may be studied on-line in the same flow channel, as different wavelengths returns different information of the interaction. E.g:

Short wavelengths of ~630 nm results in higher surface sensitivity (shorter penetration depth of the plasmon electric field, smaller detection volume).

Longer wavelengths in the Near infrared (NIR) range, ~760-820 nm results in deeper penetration depth of the plasmon electric field, sensitivity averaged over larger detection volume.

Wavelengths in the IR range~≥1.3 um further increases said penetration depth to a range suitable for detection of cellular membranes and similar biological structures.

Alternatively, one or more of said light sources 24a and 24b may be capable of selectively providing light at two or more wavelengths. This may e.g. be achieved by two or more light sources of different wavelengths arranged close together in the horizontal plane.

What is claimed is:

1. A Surface Plasmon Resonance (SPR) biosensor system comprising:
    an illumination unit arranged to selectively direct two or more wedge shaped beams of light;
    a SPR sensor surface, wherein the two or more wedge shaped beams of light from the illumination unit form respective two or more line-shaped detection areas on the SPR sensor surface transverse to the direction of light propagation, the two or more line-shaped detection areas being spaced apart from each other, wherein each wedged shaped beam is focused at a corresponding line-shaped detection area comprising a plurality of detection spots, with each of the plurality of detection spots associated with a respective flow cell for passing the analyte over the spot;
    a two-dimensional detection unit comprising a plurality of detector columns disposed along one dimension of the detection unit and a plurality of detector rows along the other orthogonal dimension of the detection unit, wherein each detector column comprises a plurality of detection elements, and each detection element corresponds to an angle of reflection;
    wherein a detection spot in one of the line-shaped detection areas forms a detection spot pair with a corresponding detection spot in a different line-shaped detection area, and the detection spot pair is imaged onto a same detector column of the detection unit.

2. The SPR biosensor system according to claim 1, wherein the illumination unit comprises static illumination optics and two or more light sources spaced apart in a direction transverse to the direction of light propagation.

3. The SPR biosensor system according to claim 2, wherein each of the two or more light sources are spaced apart a distance in the direction of light propagation such that each associated wedge shaped beam of light is focused at its corresponding line-shaped detection area on the SPR sensor surface.

4. The SPR biosensor system according to claim 2, wherein the two or more light sources comprise two or more closely mounted LEDs, ELEDs, SLDs, or laser diodes.

5. The SPR biosensor system according to claim 2, wherein the two or more light sources comprise two or more closely mounted optical fibers, waveguides, or light pipes.

6. The SPR biosensor system according to claim 5, wherein the two or more light sources continuously emit light, and their opto-coupling to optical fibers, waveguides, or light pipes includes means for alternatively switching a passage of light on and off at a frequency, in synchronization with a readout from the two-dimensional detector unit.

7. The SPR biosensor system according to claim 2, wherein the two or more light sources comprise two or more LEDs, ELEDs, SLDs, or laser diodes; and wherein beams of light from each light source, whether coming directly from each light source or via a beam collimator, a beam collector, or a beam condenser, are combined by a beam combining arrangement positioned in a light path before the static illumination optics that forms the wedge shaped beams.

8. The SPR biosensor system according to claim 7, wherein the beam combining arrangement comprises a half-transparent mirror.

9. The SPR biosensor system according to claim 7, wherein the beam combining arrangement comprises an optical body which is divided into a transparent part and a reflective part, wherein the optical body is configured to transmit a first light source light beam in a direction towards the static illumination optics while reflecting a second light source light beam in the direction towards the static illumination optics.

10. The SPR biosensor system according to claim 7, wherein the beam combining arrangement comprises an optical body divided into different reflective parts, each reflective part arranged to reflect the light beam of one light source in a direction towards the static illumination optics.

11. The SPR biosensor system according to claim 1, wherein the illumination unit comprises static illumination optics, a light source and a light beam translation unit for selectively translating a light beam from the light source in a direction transverse to the direction of light propagation.

12. The SPR biosensor system according to claim 1, further comprising an SPR evaluation unit arranged to measure relative SPR-angle shifts from combined readings of SPR-curves for light reflected from the line-shaped detection areas on the SPR sensor surface.

13. The SPR biosensor system according to claim 1, further comprising two or more flow cells associated with and for supplying interaction reagents to the detection spots.

14. The SPR biosensor system according to claim 1, wherein the illumination unit comprises two or more light sources having different wavelengths with respect to each other.

15. The SPR biosensor system according to claim 1, wherein the detection spot pair are imageable onto a same pixel column detection element in the same detector column.

* * * * *